(12) United States Patent
Rigaux et al.

(10) Patent No.: US 6,324,432 B1
(45) Date of Patent: Nov. 27, 2001

(54) ELECTRICAL NEUROMUSCULAR STIMULATOR FOR MEASURING MUSCLE RESPONSES TO ELECTRICAL STIMULATION PULSES

(75) Inventors: Pierre Rigaux, Liège (BE); Félix Buhlmann, Lausanne; Pierre-Yves Müller, Hermance, both of (CH)

(73) Assignee: Compex SA, CH-Ecublens (CH)

( * ) Notice: Subject to any disclaimer, the term of this patent is extended or adjusted under 35 U.S.C. 154(b) by 0 days.

(21) Appl. No.: 09/431,080

(22) Filed: Nov. 1, 1999

(51) Int. Cl.[7] ........................................ A61N 1/18
(52) U.S. Cl. ..................... 607/62; 607/115; 607/48; 600/546; 600/372
(58) Field of Search .................. 607/62, 48, 148, 607/115; 600/546, 554, 595, 372, 393; 128/905

(56) References Cited

U.S. PATENT DOCUMENTS

| | | |
|---|---|---|
| 4,165,750 | 8/1979 | Aleev . |
| 4,207,904 | 6/1980 | Greene . |
| 4,524,774 | 6/1985 | Hildebrandt . |
| 4,580,339 | 4/1986 | Ioffe . |
| 4,805,636 | 2/1989 | Barry et al. . |
| 4,811,742 | 3/1989 | Hassel et al. . |
| 5,070,873 | 12/1991 | Graupe et al. . |
| 5,131,401 | * 7/1992 | Westenskow et al. ............... 600/546 |
| 5,300,096 | 4/1994 | Hall et al. . |
| 5,355,883 | 10/1994 | Ascher . |
| 5,507,788 | 4/1996 | Lieber . |
| 5,540,735 | 7/1996 | Wingrove . |

FOREIGN PATENT DOCUMENTS

| | | |
|---|---|---|
| 2425865 | 12/1979 | (FR) . |
| 95/10323 | 4/1995 | (WO) . |
| 99/19019 | 4/1999 | (WO) . |

* cited by examiner

Primary Examiner—George R. Evanisko
(74) Attorney, Agent, or Firm—Sughrue, Mion, Zinn, Macpeak & Seas, PLLC

(57) ABSTRACT

The electrical stimulator includes an electrical pulse generator arranged in a case, stimulation electrodes (7) to be placed on a user's skin on the motor points of the muscles to be stimulated, each electrode (7) being connected to an electric cable (5) connector, the other end of the cable being connected in a removable manner to a signal input and/or output socket of the case for receiving the electric pulses, at least one sensor (11) for measuring the muscle reactions caused by the electric pulses, and electronic means in the case for receiving the measurements from the sensor. The sensor (11) is intrinsically linked to one of the electrodes (7) or to the connector (6). At least one conductor wire (15) of the cable connects the electrode (7) independently of the sensor (11).

Figure 1A:
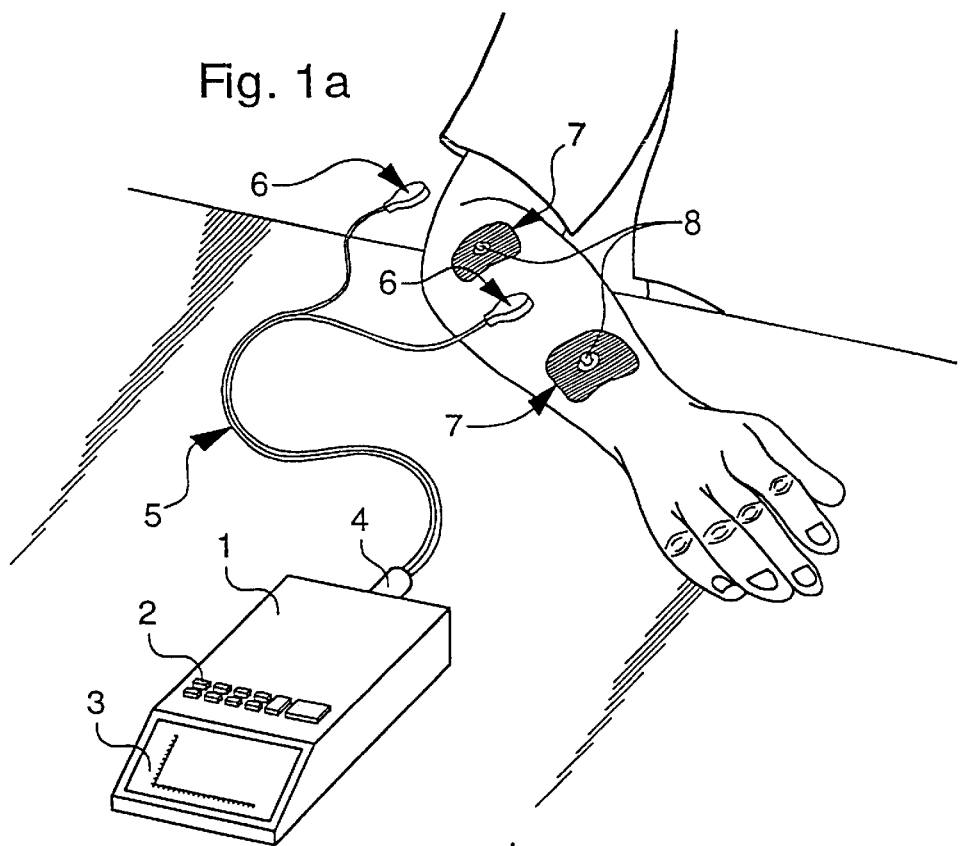

The stimulator finds application in particular in the field of sports for the passive exercising of muscles stimulated by electric pulses, or in the re-education of atrophied muscles. In this case, the sensor (11) is used to provide data as to the reactivity of the stimulated muscles and their fatigue level. This data is seen on a display of the stimulator and is used to adjust the stimulation parameters manually or automatically.

13 Claims, 3 Drawing Sheets

ELECTRICAL NEUROMUSCULAR STIMULATOR FOR MEASURING MUSCLE RESPONSES TO ELECTRICAL STIMULATION PULSES

The invention concerns an electrical neuromuscular stimulator for measuring muscle reactions generated by electrical stimulation pulses. The stimulator includes an electrical pulse generator arranged in a case, at least one pair of stimulation electrodes intended to be placed on the skin of an user in the vicinity of the motor points of the muscles to be stimulated, each electrode being connected to one end of an electric cable, the other end of which is connected to the case to receive the electric pulses from the generator, at least one sensor sensitive to the muscle reactions caused by the electric stimulation pulses and arranged for transmitting electric measuring signals representative of said muscle reactions to electronic means in the stimulator case.

The invention also concerns an electric cable and a stimulation electrode for a neuromuscular electric stimulator.

The sensor supplies data regarding the useful muscle reactions in particular in order to know the fatigue level of the electrically stimulated muscles. The measurements obtained from the sensor allow the parameters of the electric stimulation pulses to be adjusted either manually by viewing the shape of the signals received by the sensor on a display or automatically by adjusting the electric stimulation parameters as a function of the muscle fatigue. Adjusting the parameters consists in correcting either the frequency of the pulses, or the amplitude or duration of the voltage or current pulses, or the duration of muscle contraction and relaxation, or the number of contraction/relaxation cycles, or any combination of the preceding parameters.

The object of electric stimulation or electrostimulation is to control working of the muscles by the intermediary of electric voltage or current pulses as a function of programmed parameters. Each voltage or current pulse provides excitation of the nerve fibres which control the muscle fibres via the motor end-plate This excitation causes an elementary mechanical muscle response called a twitch with a duration of the order of 0.1 seconds.

The voltage or current pulse is repeated over time at an adjustable frequency. If this frequency is low, for example 10 Hz, the working power of the muscles is slight, whereas for a high frequency, for example 100 Hz, the working power of the stimulated muscle fibres is very high. This very high power corresponds to a powerful tetanic contraction. The muscle fibre twitches can no longer be separated after each pulse at this high frequency, which means that a temporal summation of the twitches occurs which leads to a tetanic contraction.

If the stimulated muscles are stimulated at a high frequency, they will tend to become tired. In this case, the exercising session consists in alternating contraction periods and rest periods. The rest phase allows the fibres to relax and recover prior to the next contraction phase.

In the medical field, electric stimulators are used to assist handicapped persons or accident victims so as to overcome deficiencies in muscular activity or to allow them to rehabilitate withered musculature. Electric current or voltage pulses are transmitted to said muscles via the electrodes placed on the skin or subcutaneously in order to make them work passively. Measurements of the muscle reaction caused by the electrically evoked twitch allows the electric pulses to be transmitted to the electrodes to be adjusted as a function of the level of the electrical or mechanical amplitude measured on the innervated muscles without thereby excessively tiring the muscles stimulated. This adjustment of the electrical parameters of the stimulator is used in particular for handicapped persons or accident victims, to prevent them being continually obliged to ask for external help when they have to move one or other of their deficient limbs.

A stimulator of this type is shown in U.S. Pat. No. 5,070,873 which discloses a control loop for the electric pulses to be supplied to the muscles to give them sufficient motricity. In a first phase, electromyographic sensors detect the voluntary muscle activity which in the case of a handicapped person is lacking. The voltage measurement obtained by the sensors represents the low contraction state of the activated muscles which leads to adjusting the electric pulses from the pulse generator to send voltage pulses adjusted to the expected reaction to the muscle motor nerves, in particular to allow automatism in the coordination of movements desired by the handicapped person.

The electromyographic sensors can be separated from the stimulation electrodes, but may also be combined therewith. In the latter case, a third electrode is necessary. If the same active surface of the electrode is used both as stimulation electrode and sensor, this involves controlling, with difficulty, the signals originating from the sensor following the electric pulses sent across the electrode.

The combination of the sensor with the electrode requires rectangular biphasic voltage pulses to be sent to perform the measurements by the sensor. It is to be noted that in this case, for voltage pulses, the stimulation current provided depends on the impedance of the electrode and the skin. This impedance is not the same from one person to another, or can vary rapidly over time in the same person, which leads to different muscle reactions for identical voltage pulses sent to the electrodes.

The use of a current pulse generator allows one to be rid of the drawbacks of a voltage pulse generator, since the pulse is kept constant whatever the impedance of the skin and the electrode, and thus allows the same number of fibres recruited for stimulation to be maintained.

One drawback of this combination of active surfaces of the sensor and the electrode lies in the fact that after the sequence of sent biphasic voltage pulses, there remains a residual voltage which can have a value of ten volts, whereas the measurement voltage drawn from the muscles by the sensor is of the order of a few millivolts. It is thus necessary to attenuate this residual voltage in order to be able to make an accurate measurement in particularly of the fatigue level of the stimulated muscles. This is why sensors separated from the electrodes provide better results than those combined as described hereinbefore.

French Patent No. FR 2 425 865 also discloses a bioelectrically controlled electric muscle stimulator. A carrier frequency generator provides an electric signal to the muscles to be stimulated which is adjusted as a function of the bioelectrical activity of the innervated muscles. With this adjustment of the electric pulses as a function of the measured muscle reaction, this stimulator offers a wide range of uses. It allows, in particular, a certain motor automatism of movements for example during sports exercising or for assisting handicapped persons.

The measurement sensors are of the electromyographical type and can also be combined with the stimulation electrodes, but in this case, since the voltage pulses sent to the muscles are mainly voltages of the sinusoidal order, drawing the EMG signals originating from the same stimulation electrodes using filters does not pose too much of a problem, which is not the case with rectangular voltage pulses.

The muscular contraction measurement means for providing data as to the state of reaction of the stimulated muscles can be performed in many ways. The measurement can be either electrical using electromyographical sensors, or mechanical followed by an electrical conversion for example using acoustic sensors (microphones). Such an arrangement is shown in U.S. Pat. No. 4,805,636 in which the vibrations of the contracting muscles are measured.

In this Patent document, two microphones are placed at different locations where the innervated muscles respond mechanically by a twitch to the voltage pulse generated by an electric pulse generator. A feedback circuit takes account of the voltage signals given by the two microphones in order to adjust the twitch or the electric pulses which the generator generates for the muscles.

Strain gauges like any other type of electric conversion mechanical sensor can be used as described in U.S. Pat. No. 5,507,788. The strain gauges are used to measure a torque developed by the stimulated muscles. They are arranged at a distance from the stimulation electrodes. The signals thereby obtained from the gauges are processed by a set of circuits in the stimulator in order to adjust the stimulation parameters of the pulse generator as a function in particular of the muscle fatigue.

The use of strain gauges can only be applied in the case where it is possible to be able to measure a torque. A sensor of this type is not, however, appropriate if measurements are made for dorsal or pectoral muscles for example, which do not involve movement of a segment.

One object of the invention is to use a structure combining a stimulation electrode with a sensor for measuring muscle reactions which overcomes the drawbacks of the stimulators described hereinbefore.

Another object of the invention consists in allowing an user to think only of placing the electrodes on the muscles as for a standard electric stimulator while in addition providing, via the sensors combined with the respective electrodes, measurements of the muscle reactions at the locations stimulated.

The objects of the invention are achieved as a result of the stimulator indicated hereinbefore which is characterised in that the sensor is mechanically connected to one of the electrodes or to the end of one of the cables on the electrode side, and in that at least one conductor wire per electric cable connects the respective electrode independently of the sensor.

The objects of the invention are also achieved as a result of the electric cable for a stimulator which is characterised in that one end of the cable on the electrode side has a connector for being connected to the structure of a stimulation electrode via removable securing means also acting as an electric contact for the active surface or surfaces of the electrode, in that the connector includes at least one portion of a muscle reaction measurement sensor, and in that it includes in an insulating sheath at least one conductor wire for connecting the active surface or surfaces of the stimulation electrode independently of the sensor.

The objects of the invention are also achieved as a result of the stimulation electrode for a stimulator which is characterised in that it comprises at least one conductive active surface for receiving the electric pulses and in that the active surface is electrically connected to removable securing means to a cable connector.

One advantage of the stimulator with the electrode and measuring sensor combination consists in facilitating the placing of said elements for example for the passive training of a sportsman using such a stimulator or for all other applications. The sportsman knows where to place the electrodes on the motor points of the muscles which he wishes to exercise. When first using such a stimulator, he has had to learn to situate the motor points for the muscles to be exercised. Through habit, he easily knows how placing them at the desired locations and thus beginning the exercising session.

The supplementary addition of a sensor with the electrode which he positions will not pose any additional problem. In addition to stimulation, he will be able to take account of the fatigue of the stimulated muscles for example on a display of the stimulator.

Likewise, if the stimulator includes means for receiving signals from the sensor able to act on the pulse generator, the electric voltage or current pulses sent to the stimulation electrodes are automatically adjusted as a function of the muscle fatigue thereby avoiding any subsequent handling by the user. The measurement signals transmitted from the sensor to the stimulation reception means either pass via a different conductor wire to the electrode conductor wire, insulated in the electric cable sheath, or using signal transmitting means without any connecting wire.

One advantage of using a sensor of the electromyographical type or with mechanical-electrical conversion of the accelerometric or acoustic type lies in the fact that they can be used for any muscle in the body. Dorsal muscles are one of the examples of muscles in which the reaction measurement is not possible using a strain gauge sensor or more generally using a torque or force sensor.

Another advantage in the use of an electromyographical sensor with an electrode consists in having two active surfaces, one for the sensor and the other for the electrode. Consequently, the muscle responses are measured while minimising the disturbances originating from the active surface of the stimulation electrode.

Another advantage of the stimulator according to the invention consists in minimising the number of electrodes combined with the measuring sensors necessary on the one hand for stimulating the muscles and on the other hand for measuring the muscle reactions. One pair of electrodes combined with at least one sensor is sufficient to stimulate the muscles at the desired locations and to provide data as to the reactions of the stimulated muscles. The conductor wires connecting the sensor and the respective electrode are regrouped in a single electric cable. The manufacturing costs are thus reduced to a minimum.

Figure 1B:
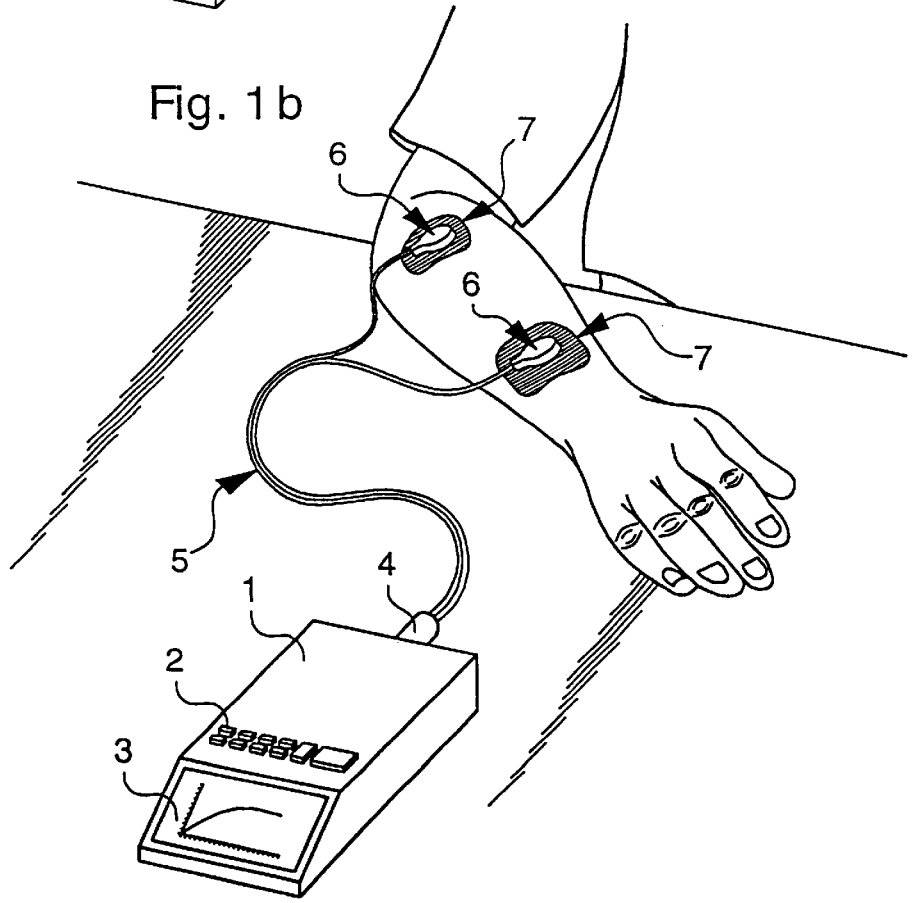
Figure 2:
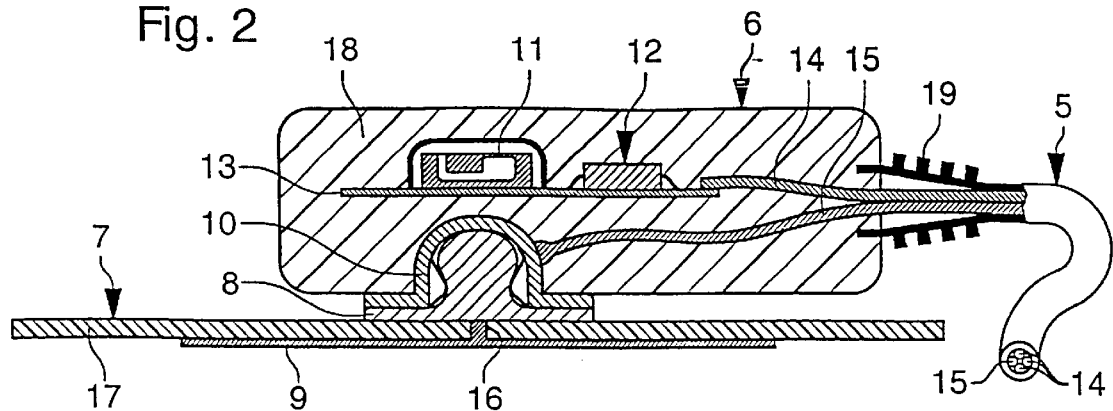
Figure 3A:
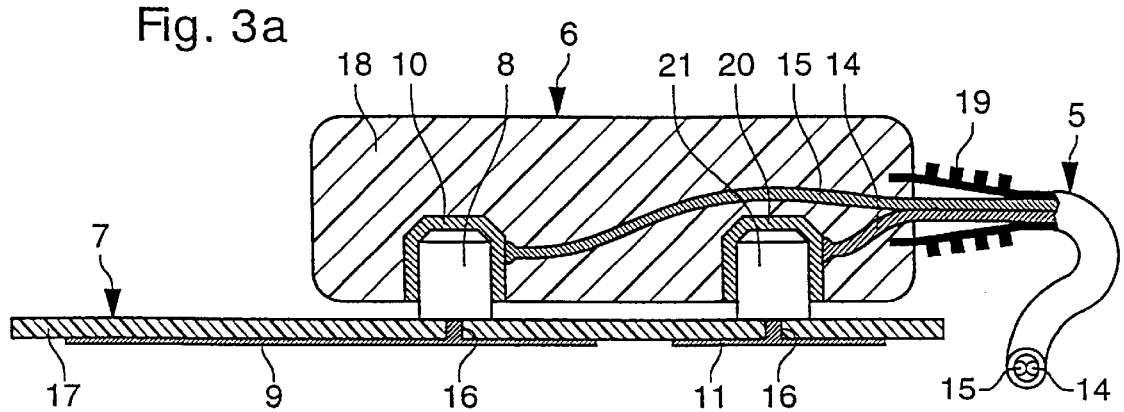
Figure 3B:
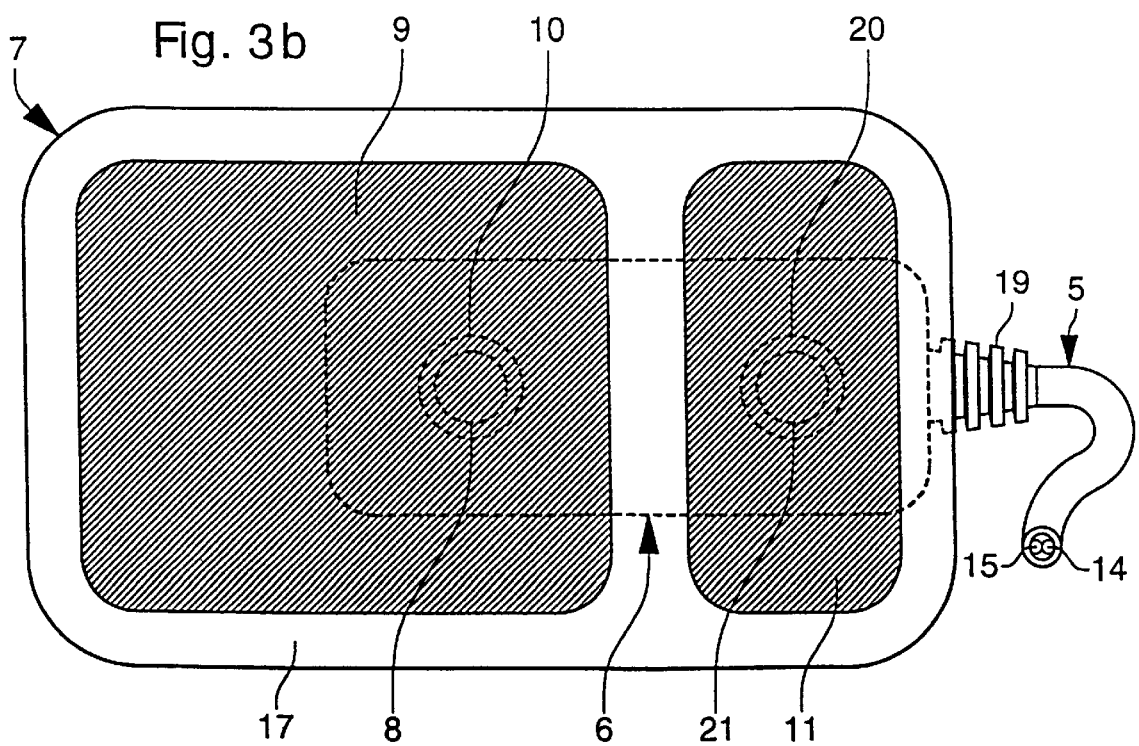
Figure 4:
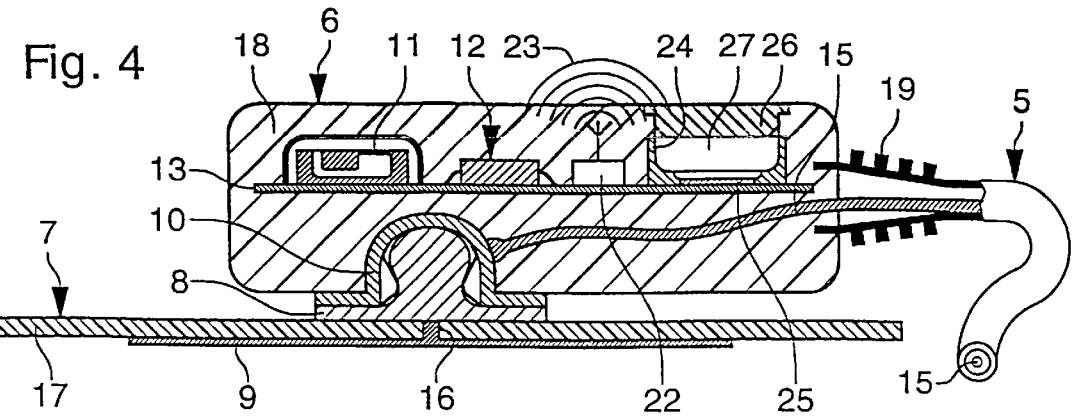
Figure 5:
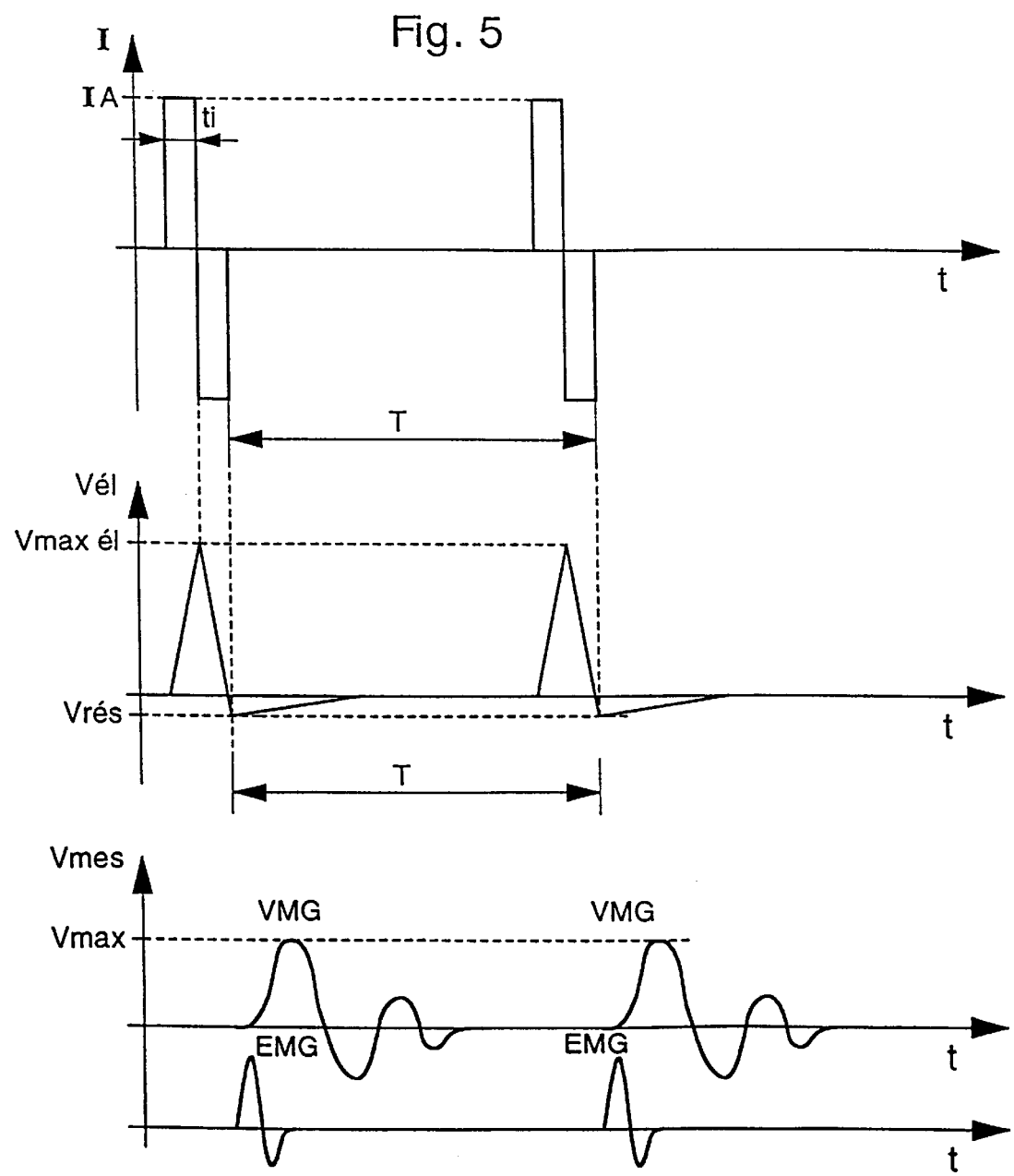

The objects, advantages and features of the stimulator will appear more clearly, in a non limiting manner, in the following description of the different embodiments illustrated by the drawings, in which:

FIGS. 1a and 1b show the stimulator before and after the connection of the electric cables to the electrodes placed on a user's skin, FIG. 2 shows a partial cross-section of a first embodiment of an electric cable connector with an integrated measuring sensor fixed onto a stimulation electrode, FIGS. 3a and 3b show a partial vertical cross-section and a bottom view of a second embodiment of an arrangement of an electromyographical sensor and electrode, FIG. 4 shows a partial cross-section of a third embodiment of an electric cable connector with an integrated measuring sensor fixed to a stimulation electrode, and FIG. 5 shows diagrams of the electric signals sent to the electrodes and the muscle response.

The stimulator described hereinafter relates preferably to a stimulator used within the field of sport and re-education in which muscle stimulation is used to exercise them passively. Rectangular current pulses are supplied to electrodes 7 placed on the skin at the motor points of the muscles to be stimulated. In response to this stimulation, the muscles contract generating a mechanical twitch. As previously described, current pulses have proved preferable to voltage pulses, since one is not dependent upon the variable impedance of the electrode and the skin of the person using the stimulator.

Current pulses are supplied over time at a given frequency. According to the pulse repetition frequency, the muscles do not have time to relax before the next pulse which increases the working power of the muscles, but on the other hand, they become tired. It is thus advantageous to know the fatigue of the stimulated muscles in order to know the state of the muscles being exercised and also to be able to take advantage of this measurement in order to adjust the stimulation parameters automatically.

In FIGS. 1a and 1b, the stimulator is represented by a case 1 enclosing in particular the current pulse generator and the means for receiving the signals originating from the sensor. On said case 1, programme selection buttons 2 are used to select the desired exercising mode as a function of the sport usually practised or the stimulation programme as a function of the pathological state (amyotrophy, hypotony, . . . ) of the muscle to be re-educated. The stimulator also includes a visual display device 3 for displaying in particular the programmes selected, the stimulation pulses, the muscle reaction measurement responses, or even statistics for the exercising sessions. Display 3 is formed for example by a liquid crystal display.

One end 4 of a pair of electric cables 5 is connected in a removable manner to one of the signal input and output sockets of stimulator case 1. Other sockets for connecting the cable are accessible for connecting several pairs of electric cables 5. From the connection to the corresponding socket, the two cables are joined so that they are not twisted when stored. They are however separated over the second half of the length of the cables so that their connector 6 can be fixed to separated electrodes 7. The connectors have complementary means which can be fixed in a removable manner to studs 8 of electrode structure 7.

Muscle reaction measuring sensors, which are not visible in FIGS. 1a and 1b, are housed in electrode structure 7 or in connector 6. The sensors are housed either in one of the electrodes or in one of the connectors or in both. Measurement of the muscle reactions usually occurs at the location where the current pulse reaches the electrodes, since the other electrode is used only for the return of the current.

A battery housed in the case supplies the stimulator with power, but it is also conceivable that the stimulator receives an external voltage supply through connection to the 220 V or 110 V mains supply via a transformer.

In FIG. 1a, the two connectors 6 are shown in a position at a distance from electrodes 7, since initially, the user places flexible self-adhesive electrodes 7 with their active surface in contact with the skin generally on the motor points. In one embodiment, the self-adhesive surrounds for example the active surface which occupies more than half of the surface of the electrode structure.

Once the electrodes have been placed on the skin, connectors 6 are fixed to electrodes 7, as can be seen in FIG. 1b. In this embodiment, connectors 6 are mounted so as to rotate freely on studs 8.

FIG. 2 shows a first embodiment of the sensor assembly with the stimulation electrode. Sensor 11 is embedded in the body 18 of connector 6 in the case in which it is obtained by moulding a plastic material. In the connector, just above complementary means 10 for the fixation thereof to stud 8 of the electrode, there is an acceleration meter forming sensor 11 arranged on a printed circuit 13 which includes all the components 12 for amplifying and processing the acceleration meter signals. The acceleration obtained by the vibration of the stimulated muscles is of the order of several 9.

Instead of acceleration meter 11, an acoustic sensor, such as a microphone can be mounted on the printed circuit to perform muscle reaction measurements.

At least two insulated conductor wires, preferably three wires 14 are fixed onto metal pads of the printed circuit to bring on the one hand the electric power supply originating from the stimulator case to the printed circuit components and on the other hand to send the muscle vibration measurement signals to the stimulator case. Another insulated conductor wire 15 is fixed to metal means 10 to bring the current pulses to the electrode. All the insulated conductor wires 14 and 15 are enclosed in a sheath of an electric cable 5.

The electrode structure is composed of a base plane 17 made of a flexible insulating material, such as a fabric or an elastomer, able to match the shape onto which it is placed, for example a user's arm. Below structure 17, a conductive film is fixed, for example by bonding or deposition of conductive particles, over a large portion of the surface of structure 17. This conductive film constitutes active surface 9 of the electrode via which the current pulses excite the motor-nerves of the muscles to be stimulated. Metal film 9 is connected through a conductive hole 16, in particular a metallised hole, made in structure 17 to metal stud 8.

The contour of the active surface of electrode 9 is coated with a selfadhesive material or a self-adhesive film so as to be able to hold electrode 7 on a user's skin. These electrodes are in principle disposable electrodes which can be used for one exercising session or for several sessions.

In an alternative embodiment, the fixing of the connector to the electrode structure via a snap fastener can be reversed by placing complementary means 10 on base plane 17 and stud 8 on connector 6.

FIGS. 3a and 3b show a second embodiment of the electrode sensor assembly. The sensor used in this embodiment is of the electromyographical type.

As in the first embodiment discussed hereinabove, connector 6 which is obtained by plastic moulding 18 can include on the interior thereof all the electronic components for processing the signals originating from the EMG sensor, but in this variant of FIG. 3a, all the electronic components are integrated in the stimulator case.

Connector 6 includes two metal pots 10 and 20 each connected, for example by soldering, to the end of a respective insulated conductor wire 14 and 15, or conversely. The pots, in addition to a length of the conductor wires and the end of a flexible sleeve 19 of electric cable 5, are moulded in plastic material 18 of the connector.

Electric cable 5 encloses, in this case, only two insulated conductor wires 14 and 15 in its insulating sheath.

The electrode structure includes, under base plane 17, a first active conductive surface 9 of the stimulation electrode and a second active conductive surface 11 which has no contact with the first active surface forming the EMG sensor. The second active surface is placed beside the first active surface. As shown in FIG. 3b, first active surface 9 is made for example with a greater dimension than second active surface 11. Around the active surfaces, the base plane is coated or covered with a self-adhesive material or film to keep it on the user's skin without using other means.

In FIG. 3b, the shape of the active surfaces is approximately rectangular, but other embodiments are entirely conceivable, for example having first active surface 9 in a circular shape placed at the centre of the electrode structure and the second active surface in the shape of a ring placed coaxially to the first surface.

Each active surface 9 and 11 is connected, through conductive holes 16, in particular metallised holes, to a corresponding metal stud 8 and 21 situated on the other side of the base plane. Since these studs 8 and 21 are chamfered on their top portion they are inserted with a certain mechanical resistance into metal pots 10 and 20 of the connector to be held therein during use. The forced insertion into the metal pots using chamfers for guiding assures a good electric contact for the transmission of the current pulses to the electrode and the electric measurement of the muscle reactions. Of course, an arrangement as shown in FIG. 2 can also be applied in this second embodiment.

Several active surfaces 9 and 11, whether for electric stimulation or measurement, can be placed under base plane 17. The active stimulation or measuring surfaces are either all electrically connected at the surface of base plane 17 through metallised holes 16, or each connected to a corresponding stud. In the latter case, a multipolar connector has to be used.

The two studs 8 and 21, and the two metal pots 10 and 20 can be designed closer together, but this involves making metal conductors on base plane 17 on the side of the connector connecting metallised holes 16 with each of studs 8 and 21.

It is also conceivable to provide studs 8 and 21 on connector 6 and metal pots 10 and 20 on base plane 17.

As previously, the electrodes have a flexible structure to match the surface of the skin on which they are placed, but there is nothing to prevent them having a rigid structure.

FIG. 4 shows a third embodiment with a sensor 11 which is identical to that shown in FIG. 2. The elements which are the same as those of FIG. 2 bear the same reference signs, and will not all be explained again.

In this third embodiment, cable 5 includes only one conductor wire 15 in an insulating sheath for bringing the electric pulses to the electrode. The measuring signals from sensor 11, processed or unprocessed in connector 6 are, however, sent by wireless measuring signal transmitting means 22 via electromagnetic waves 23 or other waves to electronic receiving means in the stimulator case. These transmitting means are placed on printed circuit 13 to receive the measuring signals from sensor 11. Waves 23 picked up by the receiving means of the case are converted into electric signals representing the measurement values of sensor 11 to be displayed on a display and/to adjust the stimulation parameters.

A power source for all the electronic components 11, 12 and 22 is provided in connector 6 in the form of an electric battery 27. The positive and negative poles of battery 27 are in contact in a battery housing with a metal wall 24 for one of the poles and with a metal base 25 for the other pole. The battery is kept in its housing by a plug 26 pressing the battery 27 against its contacts 24 and 25. This plug 26 is either screwed in, driven by force, or soldered.

Plug 26 could also be omitted, if the battery in its housing was embedded in the body of connector 6, in the event that it were not deemed necessary to change it when it becomes flat.

The connector is mounted in a removable manner on the electrode structures whether in the first, second or third embodiments to allow the user to first place the electrodes at the selected locations without being inconvenienced by the electric cables. The connector could also be integral with the electrode structure.

The means for fixing the connector to the respective electrode can take various other forms than those mentioned previously. One can envisage fixing means using a magnet housed either in the connector, or on the electrode structure, and a metal part placed either on the electrode structure or on the connector. This fixing arrangement has to guarantee the contact between metal pads between the two elements for supplying electric pulses or also for the sensor measurement.

FIG. 5 shows by way of illustration three diagrams of the signals reaching the stimulation electrodes and those drawn from the muscle reaction or response measurement whether by an acceleration meter (VMG) or an electromyographical sensor (EMG).

A current pulse is first imposed on the stimulation electrode. This pulse can be monophase, but is preferably biphase as shown in FIG. 5.

The maximum amplitude of the current $I_A$ is graduated from 0 to 120 mA. The higher this amplitude, the higher the number of muscle fibres recruited. This thus corresponds to the spatial recruitment of the fibres which perform the work required by the selected programme.

The second diagram of FIG. 5 shows the schematic shape of the skin electrode voltage. This voltage passes through a maximum value Vmax of around 100 V and a minimum value of –10 V. After the current pulse has returned to 0, there remains a residual voltage Vrés of several volts across the electrodes, which is why it is difficult to use the same active surface to measure the stimulated muscle reaction voltage variations using an EMG sensor, since the voltage measured by the sensor Vmes is of the order of a few millivolts.

The variations in voltage due to the muscle vibrations and measured by the acceleration meter (several g) and the EMG sensor for low frequency current pulses are shown in the third diagram.

At higher frequency pulses, when the muscle is contracted, the acceleration meter provides a signal only during the initial and final phases of the contraction. Conversely, the EMG sensor gives a signal even during the muscle contraction phase.

Thus, in order to obtain measurements using an acceleration meter, the acceleration signal generated can be measured either by one or more muscle twitches between the muscle contraction periods, or by the initial or final phase of the muscle contraction.

For a strength programme, the frequency of the pulses is high, whereas for an endurance programme, this frequency is low. It should be noted that for slow muscle fibres, the frequency is 30 Hz, whereas for fast muscle fibres, it is 60 Hz.

Following the description which has just been given, several other alternative embodiments of a stimulator combining an electrode with a measuring sensor can be envisaged within the reach of those skilled in the art without departing from the scope of the invention.

What is claimed is:

1. An electrical neuromuscular stimulator for measuring muscle reactions generated by electrical stimulation pulses, comprising a stimulator case, two electric cables each having at least one conductor wire, an electrical pulse generator arranged in said case of the stimulator for stimulating muscles, at least one pair of stimulation electrode structures adapted to be placed on an user's skin on motor points of muscles to be stimulated, each electrode being connected to a first end of a respective one of said two electric cables, the other end of which is connected to the case to receive the electric pulses from the generator, and at least one measuring sensor sensitive to the muscle reactions caused by the electric stimulation pulses and arranged for transmitting electric measuring signals representative of said muscle reactions to an electronic means, for processing said measuring signals, said electronic means being housed in said case, wherein the sensor is mechanically connected to one of the electrodes or to the first end of one of the cables, and wherein at least one conductor wire per electric cable connects the respective electrode independently of the sensor.

2. The stimulator according to claim 1, wherein each first end of the electric cables is securely fixed to a respective electrode structure.

3. The stimulator according to claim 1, wherein each first cable end has a connector connected to a respective electrode structure by removable fixing means.

4. The stimulator according to claim 3, wherein the removable fixing means is a snap fastening device also acting as electric contact between the connector and at least one active conducting surface of the respective electrode.

5. The stimulator according to claim 3, wherein the removable fixing means, acting also as electric contact between the connector and at least two active surfaces of the electrode, includes at least two conductive studs inserted with a certain mechanical resistance in two conductive pots, the studs forming part of the electrode structure and the pots forming part of the connector, or vice versa.

6. The stimulator according to claim 3, wherein the connector includes at least a part of said sensor sensitive to muscle reactions, and wherein each cable includes at least one conductor wire for connecting at least one active surface of the stimulation electrode independently of the sensor.

7. A stimulator according to claim 1, wherein the measuring sensor is an electromyographical sensor having at least one active conductive surface placed without electric contact beside at least one other active conductive surface of the electrode receiving the electric pulses, said active surfaces being placed on the motor points of the muscles to be stimulated.

8. The stimulator according to claim 1, wherein the measuring sensor is an acceleration meter or a microphone integrated in a connector of the first end of each cable or in a structure of one of the respective electrodes.

9. The stimulator according to claim 8, wherein the electronic means for processing the signals received from the sensor is integrated in the connector or in the electrode structure.

10. A stimulator according to claim 1, wherein the sensor is in communication with the electronic means of the stimulator via one of a wireless signal transmitting means and a wireless signal receiving means housed in a connector on the first end of the cable or in said electrode structure, or is in communication via said at least one conductor wire of the cable other than that of the electrode.

11. The stimulator according to claim 10, wherein an electric power source is housed in the connector or in the electrode structure for supplying power to electronic components of said connector or of said electrode structure for measuring muscle reactions.

12. A stimulator according to claim 1, wherein the case includes a visual display device (3) capable of displaying in particular electric stimulation programmes and data relating to the electric muscle reaction measuring signals.

13. The stimulator according to claim 1, wherein each electrode has a structure which is flexible and is adapted to match the shape onto which the structure is placed, and wherein a portion of the structure, surrounding at least one active surface of the electrode and is coated or covered with a self-adhesive material or film and is adapted to stay on the skin without using additional holding elements.

* * * * *